(12) United States Patent  
Steinhardt et al.

(10) Patent No.: US 8,142,500 B2  
(45) Date of Patent: Mar. 27, 2012

(54) VARIABLE-LENGTH OSSICULAR PROSTHESIS

(75) Inventors: Uwe Steinhardt, Hirrlingen (DE); Heinz Kurz, Dusslingen (DE); Walter Gamer, Stutensee (DE)

(73) Assignee: Heinz Kurz GmbH Medizintechnik, Dusslingen (DE)

(*) Notice: Subject to any disclaimer, the term of this patent is extended or adjusted under 35 U.S.C. 154(b) by 197 days.

(21) Appl. No.: 12/756,308

(22) Filed: Apr. 8, 2010

(65) Prior Publication Data

US 2010/0262236 A1   Oct. 14, 2010

(30) Foreign Application Priority Data

Apr. 10, 2009   (DE) .................. 10 2009 016 468

(51) Int. Cl.  
*A61F 2/18* (2006.01)

(52) U.S. Cl. .......................................................... 623/10

(58) Field of Classification Search .................. 623/10  
See application file for complete search history.

(56) References Cited

U.S. PATENT DOCUMENTS

| | | | |
|---|---|---|---|
| 3,710,399 A | 1/1973 | Hurst | |
| 4,921,498 A * | 5/1990 | Bays et al. | ............. 623/10 |
| 5,104,401 A | 4/1992 | Kurz | |
| 5,554,188 A | 9/1996 | Prescott | |
| 6,387,128 B1 | 5/2002 | Kurz et al. | |
| 6,482,144 B1 | 11/2002 | Muller | |
| 6,554,861 B2 | 4/2003 | Knox et al. | |
| 6,579,317 B2 | 6/2003 | Kurz | |
| 7,553,328 B2 | 6/2009 | Steinhardt et al. | |
| 2003/0097178 A1 | 5/2003 | Roberson et al. | |
| 2008/0208337 A1* | 8/2008 | Awengen et al. | ............. 623/10 |

FOREIGN PATENT DOCUMENTS

| | | |
|---|---|---|
| DE | 39 01 796 | 7/1990 |
| DE | 297 22 084 | 2/1998 |
| DE | 199 48 375 | 5/2001 |
| DE | 20 2005 015 944 | 12/2005 |
| DE | 10 2005 010 705 | 8/2006 |
| DE | 10 2005 027 215 | 12/2006 |
| DE | 20 2007 012 217 | 11/2007 |
| EP | 0 998 884 | 5/2000 |
| EP | 1 181 907 | 2/2002 |
| WO | 92/18066 | 10/1992 |
| WO | 02/069850 | 9/2002 |
| WO | 2008/027862 | 3/2008 |

* cited by examiner

*Primary Examiner* — Bruce E Snow  
(74) *Attorney, Agent, or Firm* — Michael J. Striker (57) ABSTRACT

An ossicular prosthesis has a first fastening element for connection to the tympanic membrane or a component of the ossicular chain, a second fastening element for connection to a further component of the ossicular chain, or directly to the inner ear, an elongated connecting element that connects the two fastening elements in a sound-conducting manner and includes an adjusting device for adjusting the axial length of the prosthesis and including at least two partial strands that extend symmetrically to the longitudinal axis of the connecting element, are extendable and/or compressible in the axial direction, are permanently plastically deformable, and are folded into a plurality of loops transversely to the longitudinal axis before being deformed. As a result, a relatively simple design of the adjusting device considerably reduces the number of different prostheses that must be kept on hand, while ensuring that the prosthesis may be optimally adapted for a specific case.

25 Claims, 10 Drawing Sheets

VARIABLE-LENGTH OSSICULAR PROSTHESIS

CROSS-REFERENCE TO RELATED APPLICATION

The invention described and claimed hereinbelow is also described in German Patent Application DE 10 2009 016 468.5 filed on Apr. 10, 2009. This German Patent Application, whose subject matter is incorporated here by reference, provides the basis for a claim of priority of invention under 35 U.S.C. 119(a)-(d).

BACKGROUND OF THE INVENTION

The present invention relates to an ossicular prosthesis that replaces or bridges at least one component, or parts of a component, of the human ossicular chain, in which the ossicular prosthesis includes, at one end, a first fastening element for mechanical connection to the tympanic membrane or a component of the ossicular chain, in particular to the limb of incus or the manubrium of malleus, and, at the other end, includes a second fastening element for mechanical connection to a further component, or parts of a component, of the ossicular chain, or directly to the inner ear, and includes an elongated connecting element that connects the two fastening elements in a sound-conducting manner, and includes an adjusting device for adjusting the axial length of the ossicular prosthesis in the axial direction of the elongated connecting element, the first fastening element being mechanically rigidly connected to one end, and the second fastening element being mechanically rigidly connected to the other, axially opposed, end of the connecting element.

A device of this type is made known in DE 20 2007 012 217 U1.

Ossicular prostheses are used in cases in which the ossicles of the human middle ear are missing or damaged, either entirely or partially, in order to conduct sound or the sound signal from the tympanic membrane to the inner ear. The ossicular prosthesis has two ends. Depending on the specific circumstances, one end of the ossicular prosthesis is fastened to the tympanic membrane, e.g., using a top plate, and the other end of the ossicular prosthesis is fastened, e.g., to the stapes of the human ossicular chain, or it is inserted directly into the inner ear. In the case of the known ossicular prostheses, sound conduction or signal transmission between the tympanic membrane and the inner ear is limited in many cases, because these known ossicular prostheses do not fully replace the natural anatomical formations of the ossicular chain.

Three types of ossicular prostheses that are used particularly frequently are stapes prostheses, partial prostheses, and total prostheses. Stapes prostheses are fixed to the incus, and extend via a piston into the inner ear. Partial prostheses typically bear via a top plate against the tympanic membrane and establish a connection to the head of the stapes. Total prostheses connect the tympanic membrane to the base of the stapes.

One of the main problems that arises in every case of reconstructing the human ossicular chain involves selecting the correct length of prosthesis. The lengths that are required vary within a range of several millimeters, due to differences in anatomy. When an ossicular prosthesis is surgically implanted, it is therefore necessary to have on hand a sufficiently large selection of prostheses having different axial lengths, or it must be possible to reduce the maximum starting length of the ossicular prostheses to the final axial length that is required.

A device, the length of which is adjustable via a clamping effect, for mechanically connecting the driver of an active hearing aid to a coupling point of the ossicular chain is described in DE 199 48 375 A1.

WO 92/18066 A1 describes a self-adjusting, passive ossicular prosthesis that includes a spring mechanism, which is complicated and very costly to manufacture, in the connection between the first and second fastening elements, which makes it possible to continually change the axial length of the prosthesis depending on the relative position of the fastening points in the middle ear. It is therefore not possible to attain a fixed, reproducibly exact length of the prosthesis even though the length is retained after the prosthesis has been surgically implanted in the middle ear. In addition, due to its very special mechanical and geometric design, the known prosthesis requires a great deal of space in the middle ear, thereby rendering it entirely unusable in many cases due to the unique conditions of a particular patient. In addition, due to the design, a considerable amount of permanent pressure builds up between the two fastening points in the middle ear after implantation, which does not exactly promote healing after surgery, and often eventually results in post-operative complications.

A passive ossicular prosthesis that has an axial length that may be varied within certain limits during surgery is described in DE 39 01 796 A1. In that case, the length is changed by bending the connecting element, which is designed as a thin gold wire, and so handling is complicated and relatively inaccurate, thereby rendering it impossible to attain the desired exact axial length of the ossicular prosthesis. In addition, the result that is attained using this technique is not always reproducible, and, once the connecting element has been bent, it is also possible for the adjusted axial length of the ossicular prosthesis to change because the connecting element springs back.

EP 0 998 884 A2 describes a passive ossicular prosthesis, in which the first connecting element, which is designed as an elongated shank, is inserted through a through-bore of the first fastening element, which is designed as a top plate, until a desired shank length between the first and second fastening elements is attained. The shank is then fixed in this position by constricting the through-bore in the top plate, and the part of the shank that extends past the top plate is trimmed off. One therefore easily obtains a prosthesis that has the particular length that is desired or required, and that remains exactly the same, after surgery in particular.

DE 10 2005 010 705 B3 makes known an ossicular prosthesis, in which an intraoperative variability of the prosthesis length is attained by virtue of the fact that the elongated connecting element is designed in the form of a ball chain. During surgery, the ball chain is inserted through a receiving opening in the first fastening element via a certain number of balls. The ball chain is then fixed in the receiving opening of the fastening element using resilient segment elements that clamp onto either side of the ball chain, and the overhanging part of the ball chain that extends through the receiving opening is cut off, and so the prosthesis ultimately has exactly the desired axial length. In a similar manner, the length variability is also attained using an ossicular prosthesis as described in DE 20 2005 015 944 U1, in which case a trimmable ball chain is likewise used as the connecting element, but the receptacle in the first fastening element has a different design.

A further passive ossicular prosthesis having an intraoperatively variable axial length is described in U.S. Pat. No.

3,710,399. In that case, a two-pieced connecting element is used between the two fastening elements; the two-pieced connecting element includes two parallel, straight wire pieces, one of which extends away from the first fastening element, and the second of which extends away from the second fastening element. The two wire pieces may be connected to the particular other wire piece using wire loops at their ends, or they may be inserted into a type of connecting coupling having two parallel longitudinal bores for the two wire pieces. In the first case, it is not possible, however, to exactly adjust the fixing position and, therefore, the relative position of the two wire pieces, thereby rendering it impossible to adjust the length of the prosthesis in an exact and reproducible manner. In the second case, once the wire pieces have been inserted into the connecting coupling, the relative positions of the wire pieces may tilt, flex, or become displaced, thereby likewise making it difficult or impossible to exactly adjust the axial length of the prosthesis.

Another technique for adjusting the length of a passive ossicular prosthesis is made known in DE 10 2005 027 215 A1. This prosthesis is designed exclusively for use in the situation of stapes surgery, and so a plunger-shaped piston is always provided as the second fastening element. A receiving mechanism is located in this piston, into which the shank-shaped connecting element will be inserted in the axial direction. Leaf springs that are spread radially apart by the connecting element have an arresting effect in a desired relative position between the connecting element and the second fastening element. Aside from the fact that an exactly reproducible adjustment of a desired axial length of the prosthesis is therefore not always guaranteed, the scope of application of this ossicular prosthesis is limited to surgery of the stapes, in the case of which a direct connection to the inner ear is attained via the piston. However, if a bell, piston, clip, or flat shoe will be used as the second fastening part, for connection to another part of the ossicular chain, then this known prosthesis is not usable. If the intention is to form a related receiving mechanism in the second fastening part, then, due to geometry, it functions only in a piston and never in bell, flat shoe, or even in a clip.

The variable-length ossicular prosthesis described in DE 297 22 084 U1 likewise covers a scope of application that is greatly limited; instead of a shank-shaped connecting element, this variable-length prosthesis includes three segment elements that may be snapped off in the manner of a stand, one end of which leads into a bell-shaped or piston-shaped body for fastening to the stapes, and the other end of which leads into a top plate for placement against the tympanic membrane. This design may be used exclusively in combination with a plate-type fastening element, i.e., only when coupling to the tympanic membrane. Another disadvantage of this prosthesis is the fact that it does not include a defined shank as the connecting element between the two fastening elements, and so the prosthesis may shift or flex transversely to the longitudinal axis of the prosthesis if axial force is not introduced absolutely exactly.

The ossicular prosthesis described in U.S. Pat. No. 5,554, 188 likewise includes a connecting element that is designed as a two-pieced shank, in which the first, rod-shaped section may be inserted into a receiving bore of the second section, which is designed as a receiving part, and may be displaced axially in the bore. To attain a desired axial length of the prosthesis, the rod-shaped first section is trimmed from a maximum starting length to a suitable end length, and it is inserted into the second section until it stops. By designing the inner diameter of the receiving bore accordingly relative to the outer diameter of the first section, a frictional clamping of the first and second sections should bring about a certain fixation of the prosthesis length, the actual fixation being attained by virtue of the fact that the parts of the prosthesis that may move in opposite directions are unable to move very far apart from one another after surgical implantation in the middle ear, due to their being stopped at the two fastening points. It is therefore impossible to ensure that a length of the prosthesis will always remain exactly the same.

In the case of the passive ossicular prosthesis described in US 2003/0097178 A1, the receiving part also includes a cavity that is open in the direction toward the insertion part and extends in the axial direction of the connecting element; the connecting element is designed to have a variable length in the axial direction between the receiving part and the insertion part, and the specific axial lengths of the connecting element of a specific ossicular prosthesis are fixed by clamping the insertion part to the receiving part in a desired relative coaxial insertion position. In principle, it is therefore possible to attain a desired, defined length of the prosthesis even before it is clamped between the two fastening points; this length is also fixedly retained after surgery, e.g., by inserting a second fastening element, which is designed as a piston, through a perforated base of the stapes.

Finally, DE 20 2007 012 217 U1, which was cited above, makes known an ossicular prosthesis of the type in question, in which the clamping force, in the clamped state, between the receiving part and the insertion part is selected to be considerably greater than the maximum external forces that occur naturally in the middle ear in the region of the ossicles. This makes it possible to vary the length of the passive ossicular prosthesis "in situ" or intraoperatively, and large selections of prosthesis having different lengths do not need to be kept on hand during every surgical procedure. In addition, it is particularly simple to adjust the particular length of the prosthesis that is desired, and, therefore, the handling is likewise particularly simple. Due to the selection of the clamping force described above, subsequent, post-operative and undesired changes in length and/or position of the prosthesis are reliably prevented. In addition, this known ossicular prosthesis may be used universally in all feasible types of couplings in the middle ear space, and it is not limited to a certain class of operations, while, e.g., the prosthesis described in above-cited DE 10 2005 027 215 A1 may only be used exclusively in the situation of stapes surgery. However, these advantages are attained via a relatively complicated, mechanical design of the adjusting device in the connecting element of the prosthesis, a level of production outlay that is considerable by nature, and resultant high manufacturing costs.

SUMMARY OF THE INVENTION

In contrast, the object of the present invention is to improve a generic, variable-length, middle-ear prosthesis of the type described initially using the simplest technical means possible, in a simple and cost-favorable manner such it is possible to very considerably reduce the number of different prostheses that must be kept on hand intraoperatively, while ensuring that the prosthesis may be optimally adapted for a specific case, and to replace the complex design of the adjusting device of the ossicular prosthesis made known in DE 10 2005 027 215 A1 by a substantially simpler mechanical design.

According to the present invention, this object is attained in a manner that is surprisingly simple yet effective in that the adjusting device includes at least two partial strands that extend symmetrically to the longitudinal axis of the connecting element, are extendable and/or compressible in the axial direction, are permanently plastically deformable, and are folded into a plurality of loops transversely to the longitudinal axis, at least before they are deformed.

Due to the plastic deformability—which results from the geometry of the adjusting device, the geometry being designed according to the present invention and ensuring that the length of the prosthesis remains constant after deformation—the range within which the length of the ossicular prosthesis may be adjusted is very wide, thereby ensuring that typically only one embodiment of the ossicular prosthesis according to the present invention need be kept on hand for every type of prosthesis having a different design of the fastening elements, and which may then be used to intraoperatively attain any length of prosthesis that is required for a particular patient. In addition, the extremely simple design, according to the present invention, of the adjusting device results in a considerable reduction of manufacturing costs. Likewise, the handling required by the operating surgeon to adjust the length for a specific patient is simpler than it is for most known prostheses.

In very particularly preferred embodiments of the ossicular prosthesis according to the present invention, at least one, and preferably a plurality of connecting segments extend transversely to the longitudinal axis and connect one loop of a partial strand to a loop of a parallel partial strand. As a result, when the adjusting device is pulled apart or compressed, the parallel partial strands are held in an exactly defined distance relative to one another at certain points, and so the adjusting device has an exactly specifiable geometry after it has been plastically deformed.

In advantageous embodiments, in order to obtain the greatest possible bandwidth of attainable axial lengths of an ossicular prosthesis according to the present invention, every partial strand includes at least three loops.

One class of embodiments of the ossicular prosthesis according to the present invention is characterized by the fact that, in the delivered state of the ossicular prosthesis, the loops of the adjusting device are folded tightly together and may be pulled apart by an operating surgeon in the direction of the longitudinal axis of the elongated connecting element in order to attain a desired axial length of the prosthesis, and, once the prosthesis has been implanted in the patient's middle ear, the loops remain, plastically deformed, in this pulled-apart state.

In an alternative class of embodiments, in the delivered state of the ossicular prosthesis, the loops of the adjusting device are pulled apart and may be compressed by an operating surgeon in the direction of the longitudinal axis of the elongated connecting element in order to attain a desired axial length of the prosthesis. Once the prosthesis has been implanted in the patient's middle ear, the loops remain, plastically deformed, in this compressed state.

In practical application, the embodiments of the ossicular prosthesis according to the present invention that prove successful are those in which the loops of the partial strands of the adjusting device are folded in a serpentine, meandering, or accordion-like manner.

To attain an even, defined extension and compression of the adjusting device during plastic deformation, in one class of embodiments, the loops of the adjusting device that extend transversely to the longitudinal axis of the elongated connecting element each have the same maximum extension.

In an alternative class of embodiments, axially opposed loop pairs of the adjusting device have maximum extensions that differ transversely to the longitudinal axis of the elongated connecting element, in particular that continually increase or decrease from one axial end of the adjusting device to the other axial end. It is therefore possible to specify a certain order in which the individual loops become deformed when the adjusting device is extended or compressed. The loops having the greatest maximum extension are typically the softest, in terms of their plastic deformability, and therefore deform first when force is applied.

In a particularly simple and compact class of embodiments of the ossicular prosthesis according to the present invention, the adjusting device itself is the elongated connecting element.

In an alternative class of embodiments, the elongated connecting element is designed as a shank, as usual.

Developments of these embodiments are preferred in which the adjusting device is integrated in the shank, and a connecting piece for the first fastening element, and a connecting piece for the second fastening element are located on the two axial ends of the adjusting device, thereby giving the prosthesis a certain level of dimensional stability in the axial direction.

Embodiments of the ossicular prosthesis according to the present invention that are very particularly advantageous are those in which an engagement device is provided on each of the two axial ends of the adjusting device, preferably with axial clearance to the first fastening element and to the second fastening element, on which a non-positive or form-fit connection may be created using a condition instrument, e.g., tweezers or pincers, in order pull the adjusting device apart or compress it, via the application of force, in the direction of the longitudinal axis of the connecting element.

The prosthesis will be designed according to the particular defect to be eliminated or at least ameliorated in terms of its effect on the patient via use of the inventive ossicular prosthesis. In a few embodiments of the present invention, the first fastening element will include a top plate designed to be placed against the tympanic membrane. In many embodiments, the prosthesis may be attached, e.g., to the limb of incus or to the stapes, or it may be inserted directly into the inner ear. In this context, an embodiment is advantageous in which the ossicular prosthesis is located at the end of the hammer (=umbo) or directly adjacent thereto, thereby resulting in the greatest leverage for the mechanical transmission of sound via motions that occur in the artificial or natural ossicular chain.

One class of embodiments of the inventive ossicle prosthesis is characterized by the fact that the second fastening element is designed as a plate, a sleeve, a loop, a closed bell, a bell having one or two slots, or as a clip for mechanical connection to a further element of the ossicular chain.

In developments of these embodiments, the prosthesis is fastened via a top plate to the tympanic membrane and via the second fastening element to the incus or stapes.

Alternative embodiments may provide that the ossicular prosthesis is coupled via its end to which the second fastening element is attached via perforation of the stapes (stapedectomy or stapedotomy), and/or by opening up the human cochlea (=cochleotomy), to which the top plate is attached at the opposite end, directly to the inner ear, using a plunger, in particular.

Once the prosthesis has been surgically implanted in the middle ear and the tympanic membrane has been closed, the recovery phase begins. Scars form during this period, and they produce unforeseeable forces which can cause the prosthesis to move out of its localized position. When there is a stiff connection between a top plate and the connecting element, increased pressure peaks may result between the edge of the top plate and the tympanic membrane, or the graft between the tympanic membrane and the top plate. These pressure peaks can be so high that penetration or extrusion through the tympanic membrane would result. For this reason, it is very helpful for the prosthesis to have a certain amount of post-surgical mobility, so that the top plate may automatically adapt, post-operatively, to the position of the tympanic membrane. Since, in addition, the unique anatomical features of the ear, such as the position, shape and size of the stapes, incus, hammer and tympanic membrane vary, it is very advantageous when ossicular prostheses are not designed to be rigid, but rather that they have a certain amount of flexibility or variability.

In the case of the ossicular prosthesis according to the present invention, the connecting element between the two fastening elements is typically designed as an elongated shank, as is well known from the related art. To attain the increased flexibility and variability of the prosthesis described above, it is possible according to a particularly preferred embodiment of the present invention, and as described extensively, e.g., in EP 1 181 907 B1, for at least one ball joint to be provided in the elongated connecting element. In terms of particularly high post-operative mobility of the prosthesis, developments are particularly advantageous in which the elongated shank includes a large number of further rotary elements which abut each other, preferably in the form of a ball joint chain.

Embodiments of the present invention are also possible in which the prosthesis or parts thereof are composed of biocompatible plastics, particularly silicone, polytetrafluoroethylene (PTFE) or polyetheretherketone (PEEK), and/or fibrous composite materials, in particular carbon fibers. These materials make it possible to prevent post-operative rejection reactions in most cases.

The ossicular prosthesis, according to the present invention, or parts thereof may be made of titanium and/or gold and/or tantalum and/or steel, and/or an alloy of these stated metals. It is known that titanium, in particular, in addition to being stiff and having excellent sound-conducting properties, also exhibits excellent biocompatibility with the human ear.

In terms of the post-operative position adjustment described above, embodiments of the present invention are advantageous in which the prosthesis or parts thereof—in particular one of the fastening elements—are composed of a material having memory effect or superelastic properties, Nitinol in particular, as is known, e.g., from WO 02/069850 A1 or U.S. Pat. No. 6,554,861 B2.

As an alternative or in addition thereto, in further embodiments, parts of the ossicular prosthesis according to the present invention may be composed of a ceramic material.

In addition to the post-operative shifting of position, a further problem results once ossicular prostheses have been implanted: The middle ear of the human body may be described as a "semi-open region". Any implantation material that is inserted in the body within the scope of reconstruction of the middle ear and its structures thereby undergoes a particular stress that predominates in a contaminated and infected environment, and which typically attacks the material. Since the objective of implanting an ossicular prosthesis must always be to enable the implant to remain in the patient's middle ear for as long as possible without complications occurring, a sustained attack on the material may result in damage being done to the prosthesis and/or in a local infection. Neither of these consequences is tolerable. In a further particularly preferred embodiment of the present invention, to permanently prevent damage from occurring to the implantation material or the surrounding tissue, the surface of the ossicular prosthesis is coated entirely or at least in sections with a biologically active coating, in particular a growth-inhibiting and/or growth-promoting and/or antibacterial coating.

In the case of the ossicular prosthesis according to the present invention, a fastening element that is designed as a top plate should always have a growth-promoting coating, but a fastening element that leads directly into the inner ear, e.g., in the form of a piston, should have a growth-inhibiting coating.

According to a particularly preferred embodiment of the ossicular prosthesis according to the present invention, the mass distribution of the individual parts of the prosthesis is calculated depending on a desired, specified or specifiable frequency response of sound conduction in the middle ear. This allows the sound propagation properties to be mechanically tuned to a certain extent using a custom-made ossicular prosthesis without a great deal of additional technical complexity.

In special embodiments, a tuning effect of this type may be attained, e.g., by fastening at least one additional mass to a part of the ossicular chain or the prosthesis depending on a desired, specifiable frequency response of sound conduction in the middle ear. In advantageous developments of these embodiments, the additional mass is fastened to a part of the ossicular chain or the prosthesis using a clip. The additional mass and/or clip may also be coated with a biologically active coating.

Finally, a further embodiment of the present invention is characterized by the fact that the prosthesis is connected to an active vibrating part of a hearing aid which is active and implantable, in particular. This also enables further hearing damage caused by the use of modern electronic devices to be prevented or at least ameliorated in terms of its effect, and a physical connection of the ossicular prosthesis to the outside world does not cause a problem—due to the coating described above, when the coating is antibacterial in design—that would result from the increased introduction of bacteria into the region of the middle ear.

Further features and advantages of the present invention result from the detailed description of embodiments of the invention presented below with reference to the figures in the drawing which shows the details that are essential to the present invention. Further features and advantages of the present invention also result from the claims. The individual features may be realized individually, or they may be combined in any possible manner in different variants of the present invention.

Embodiments of the present invention are depicted in the schematic drawing and are described in greater detail in the description that follows.

BRIEF DESCRIPTION OF THE DRAWINGS

FIGS. 1a, 1b through 5a, 5b of the drawing are subdivided into groups of two. The "a" figures each contain a schematic spacial depiction of an embodiment of the ossicular prosthesis according to the present invention, and the "b" figures show a vertical longitudinal sectional view through the embodiment that corresponds to the particular "a" figure. For the rest, elements having the same design and/or the same function are labeled in the drawing using the same reference numerals.

The drawing contains:

DESCRIPTION OF THE PREFERRED EMBODIMENTS

The five embodiments of ossicular prosthesis 10; 20; 30; 40; 50 according to the present invention, which are depicted schematically and using different detail in the figures, each includes, at one end, a first fastening element 11; 21 which is used to mechanically connect the prosthesis to the tympanic membrane or a component of the ossicular chain. Attached to the other end of ossicular prosthesis 10; 20; 30; 40; 50 is a second fastening element 12; 22; 32 for mechanically connecting the prosthesis to a further component or parts of a component of the ossicular chain, or for insertion directly into the inner ear. Located between the two is an elongated connecting element 13; 23; 33; 43; 53 that connects fastening elements 11; 21 and 12; 22; 32 in a sound-conducting manner.

Each connecting element 13; 23; 33; 43; 53 includes one adjusting device 14; 24; 34; 44; 54 for adjusting the axial length of an individual ossicular prosthesis 10; 20; 30; 40; 50 in the axial direction of the elongated connecting element 13; 23; 33; 43; 53, first fastening element 11; 21 in each case being mechanically rigidly connected to one end, and second fastening element 12; 22; 32 in each case being mechanically rigidly connected to the other, axially opposed, end of connecting element 13; 23; 33; 43; 53.

According to the present invention, adjusting device 14; 24; 34; 44; 54 includes at least two partial strands that extend symmetrically to longitudinal axis a of connecting element 13; 23; 33; 43; 53, that are extendable and/or compressible in the axial direction, that may be permanently plastically deformed to establish the axial length of ossicular prosthesis 10; 20; 30; 40; 50, and that are folded into a plurality of loops 15a', 15b', 15c', 15a", 15b", 15c"; 25a', 25b', 25c', 25a", 25b", 25c"; 35a', 35b', 35c', 35a", 35b", 35c"; 45a', 45b', 45c', 45a", 45b", 45c" that extend transversely to longitudinal axis a before they are deformed.

In all of the embodiments shown in the drawing, connecting segments 16a, 16b that extend transversely to longitudinal axis a are provided, each of which connects one loop 15a', 15b', 15c'; 25a', 25b', 25c'; 35a', 35b', 35c'; 45a', 45b', 45c' of a partial strand to a loop 15a", 15b", 15c"; 25a", 25b", 25c"; 35a", 35b", 35c"; 45a", 45b", 45c" of a parallel partial strand. In addition, every partial strand includes exactly three loops 15a', 15b', 15c' or 15a", 15b", 15c"; 25a', 25b', 25c' or 25a", 25b", 25c"; 35a', 35b', 35c' or 35a", 35b", 35c"; 45a', 45b', 45c' or 45a", 45b", 45c", which has proven in practical application to be favorable. Other embodiments of the present invention, which are not depicted in the drawing, may include fewer loops or more loops. Loops 15a', 15b', 15c', 15a", 15b", 15c"; 25a', 25b', 25c', 25a", 25b", 25c"; 35a', 35b', 35c', 35a", 35b", 35c"; 45a', 45b', 45c', 45a", 45b", 45c" of the partial strands of adjusting device 14; 24; 34; 44; 54 may be folded in a serpentine, meandering, or accordion-like manner.

All of the embodiments of the present invention that are presented in the drawing are also alike in that, on each of the two axial ends of adjusting device 14; 24; 34; 44; 54—preferably with axial clearance to first fastening element 11; 21 and to second fastening element 12; 22; 32—an engagement device 17a, 17b is provided, on which a non-positive or form-fit connection may be created using a condition instrument, e.g., tweezers or pincers, in order pull adjusting device 14; 24; 34; 44; 54 apart or to compress it, via the application of force, in the direction of longitudinal axis a of connecting element 13; 23; 33; 43; 53.

Figure 1A:
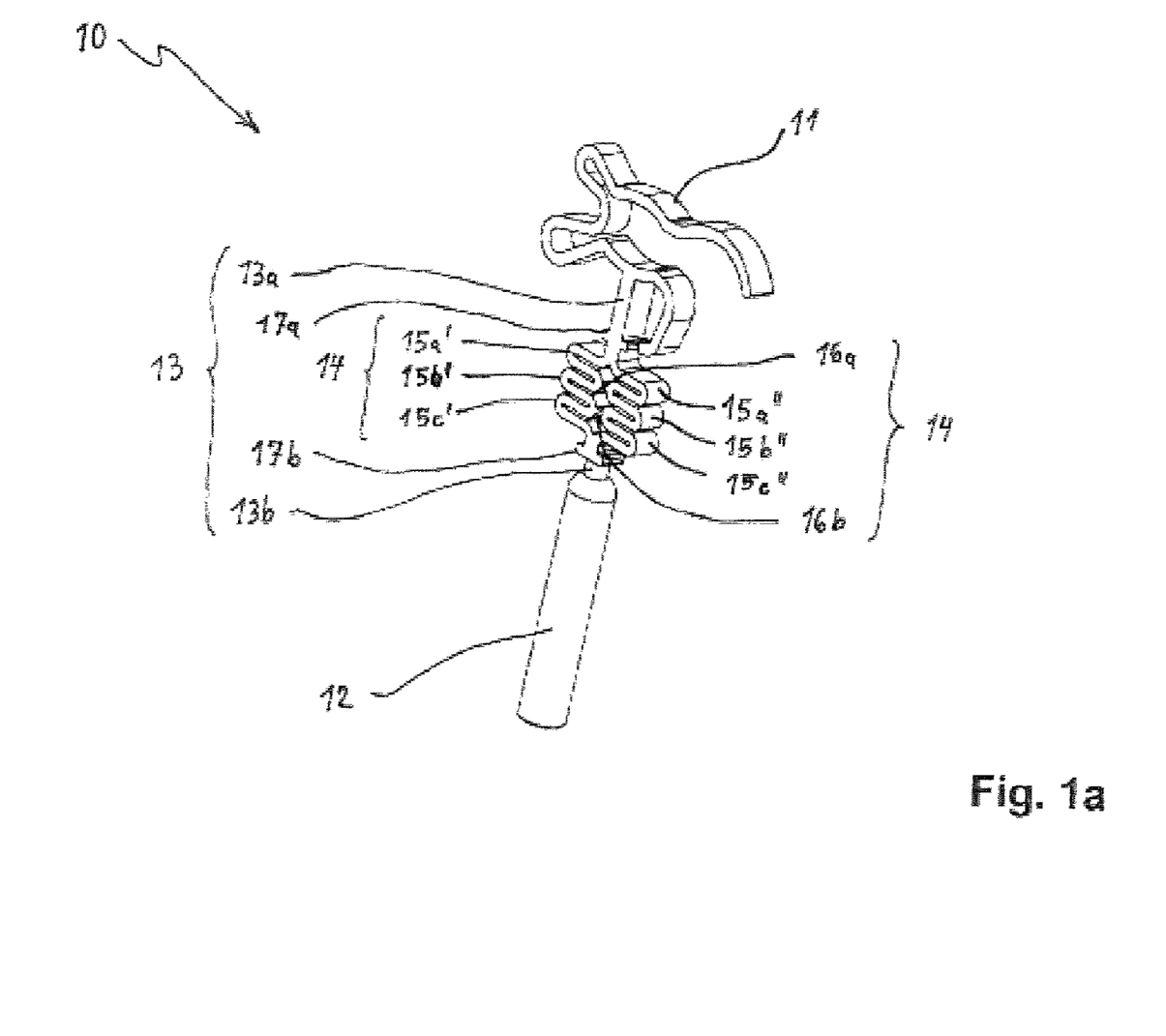
FIGS. 1a,b show an embodiment of the ossicular prosthesis, according to the present invention, that includes a clamp-shaped first fastening element, an adjusting device that includes closely folded-together loops that each have the same transverse extension, and a piston-shaped second fastening element.
Figure 1B:
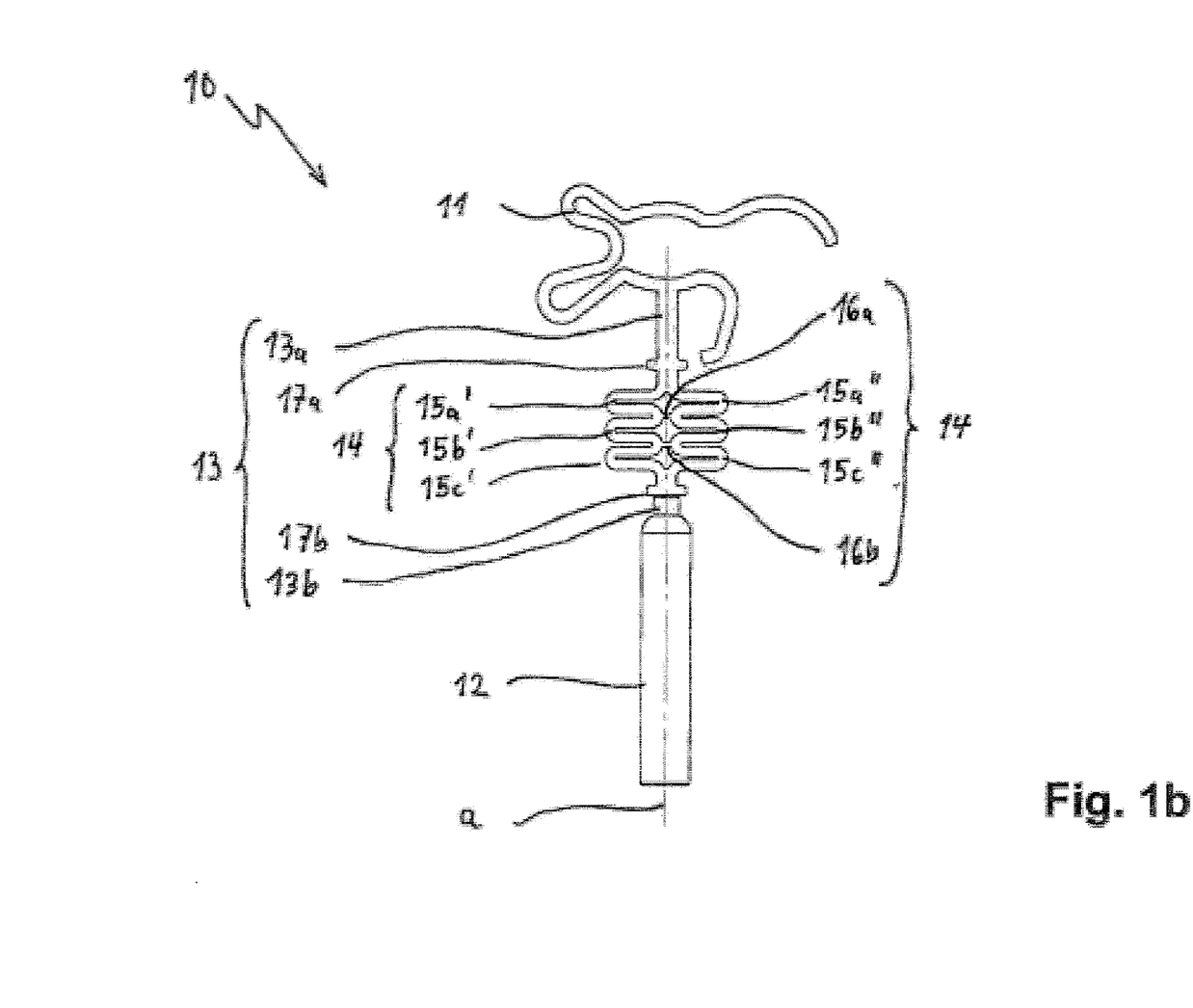
Figure 2A:
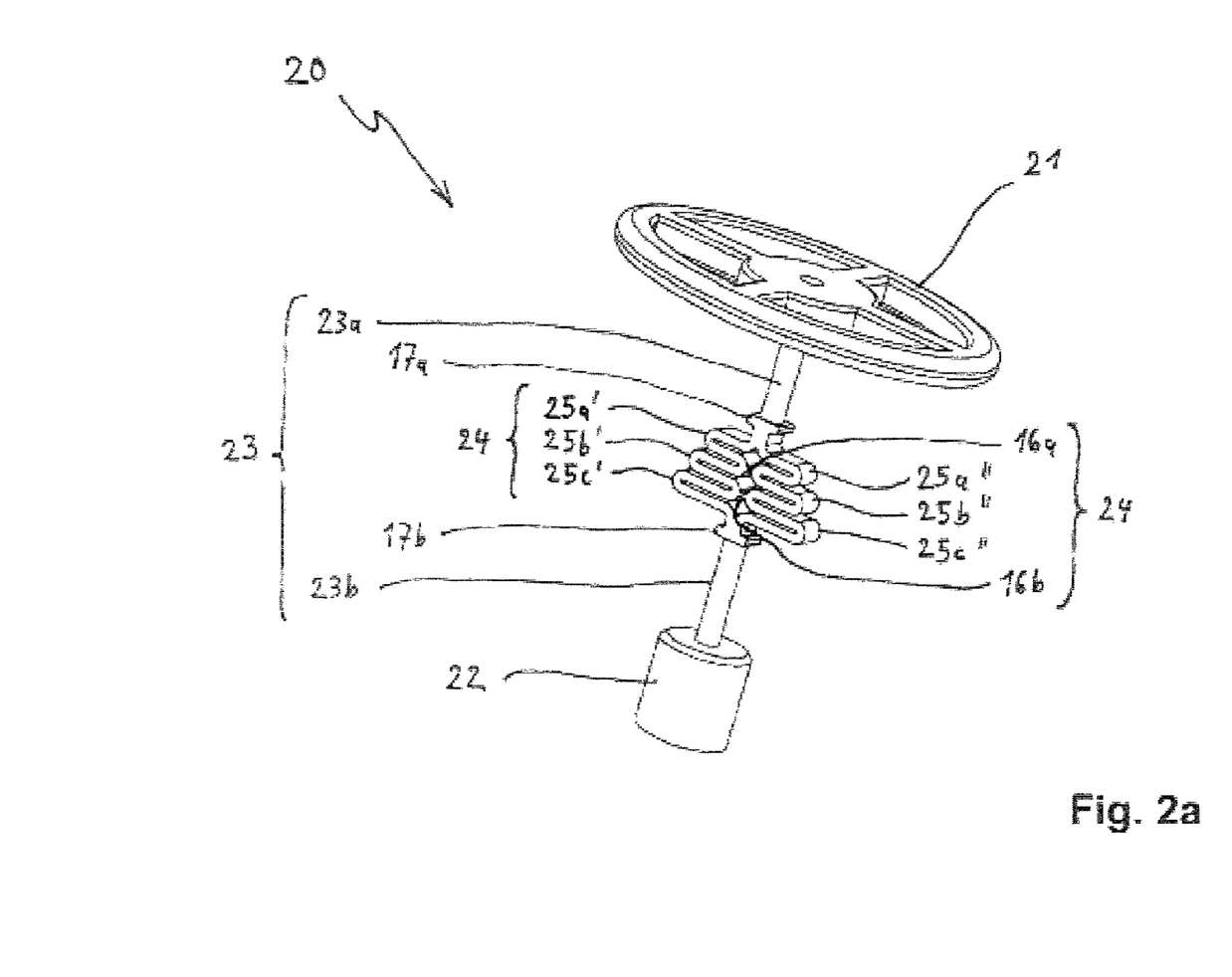
FIGS. 2a,b show an embodiment that includes an annular first fastening element that is designed as a tympanic membrane top plate, an adjusting device that includes closely folded-together loops that each have a different transverse extension, and a piston-shaped second fastening element.
Figure 2B:
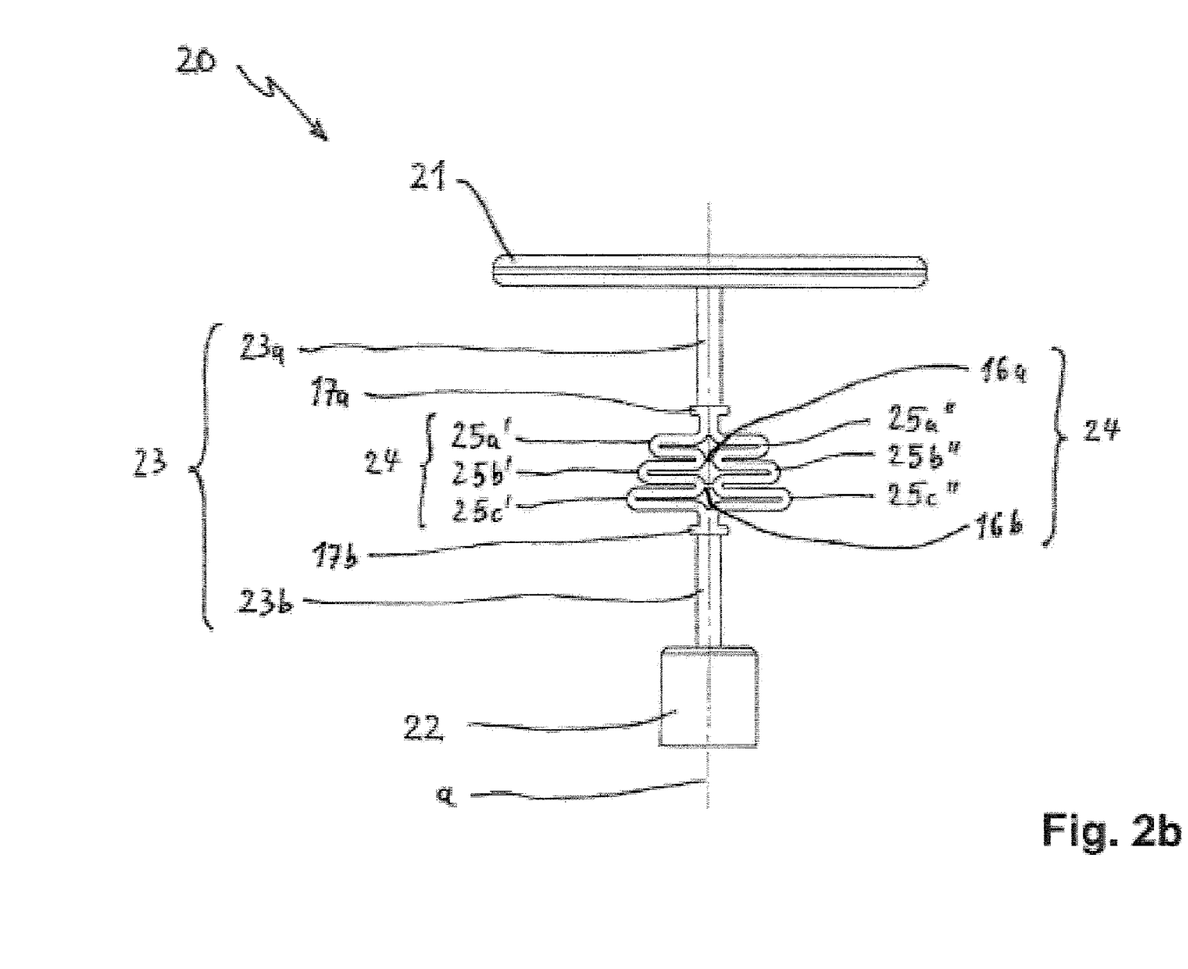

The embodiment shown in FIGS. 1a-b includes a first fastening element 11 in the form of a clamp which may be clipped, e.g., onto the limb of incus or to another component of the ossicular chain. In this embodiment, second fastening element 12 is designed, at the end opposite the clamp, as a piston for use to couple ossicular prosthesis 10 directly to the inner ear. The same design of the fastening elements is likewise shown in the embodiments of ossicular prostheses 40 and 50 as depicted in FIGS. 4a-b and 5a-b.

Figure 3A:
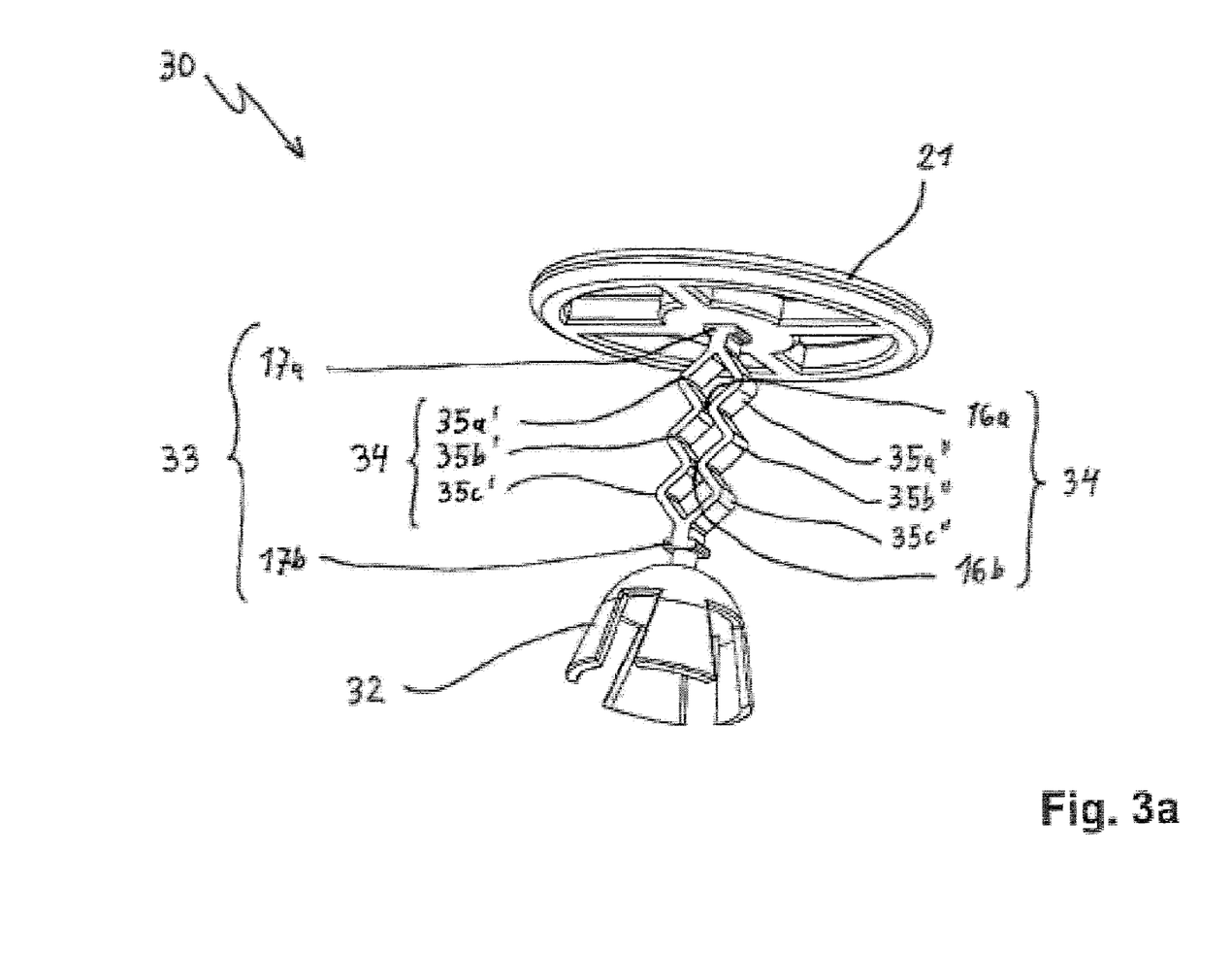
FIGS. 3a,b show an embodiment that includes a tympanic membrane top plate as the first fastening element, an adjusting device that, in its original state, is pulled apart in the manner of an accordion, and that, without further shank parts, forms the elongated connecting element, and including a slotted bell as the second fastening element.
Figure 3B:
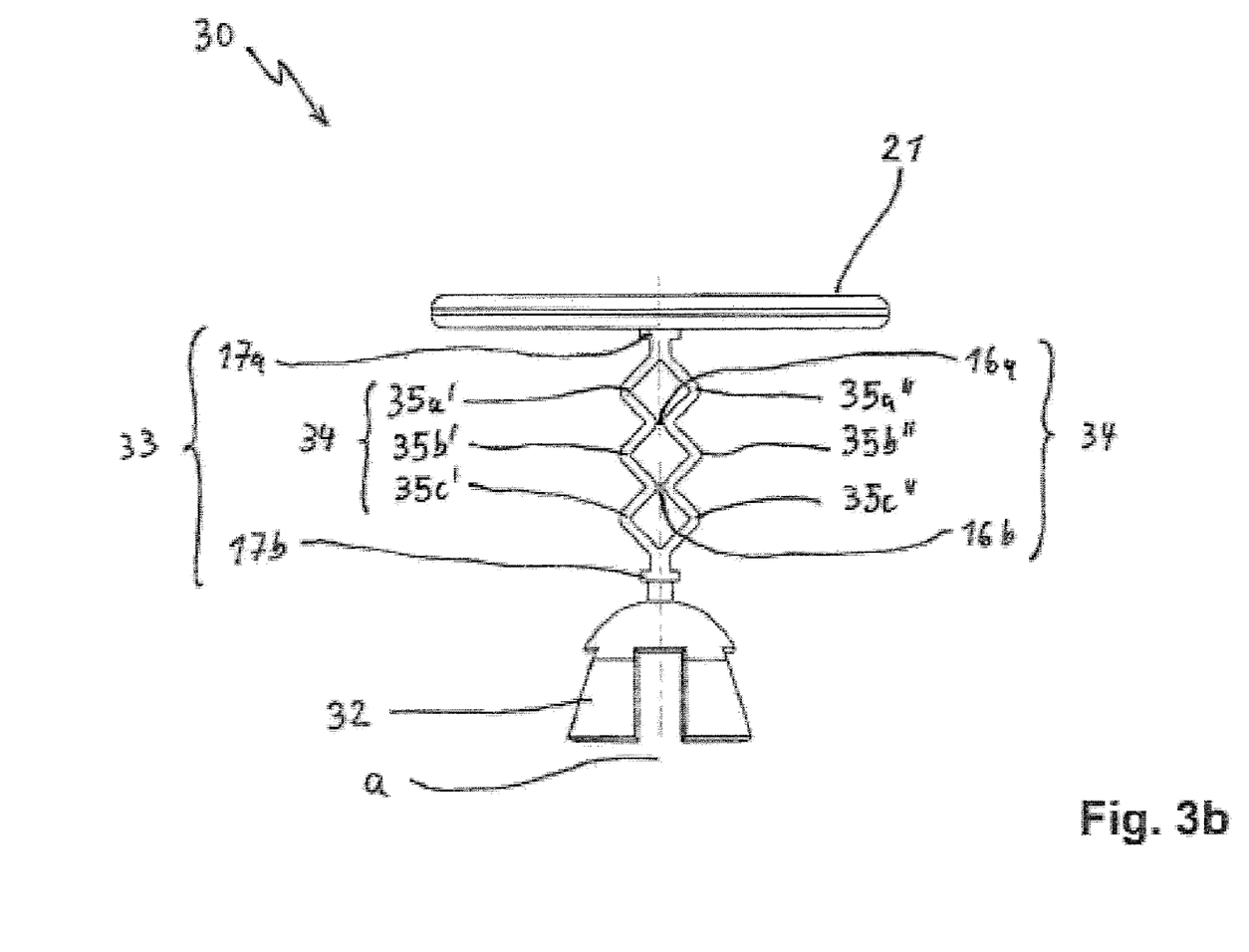
Figure 4A:
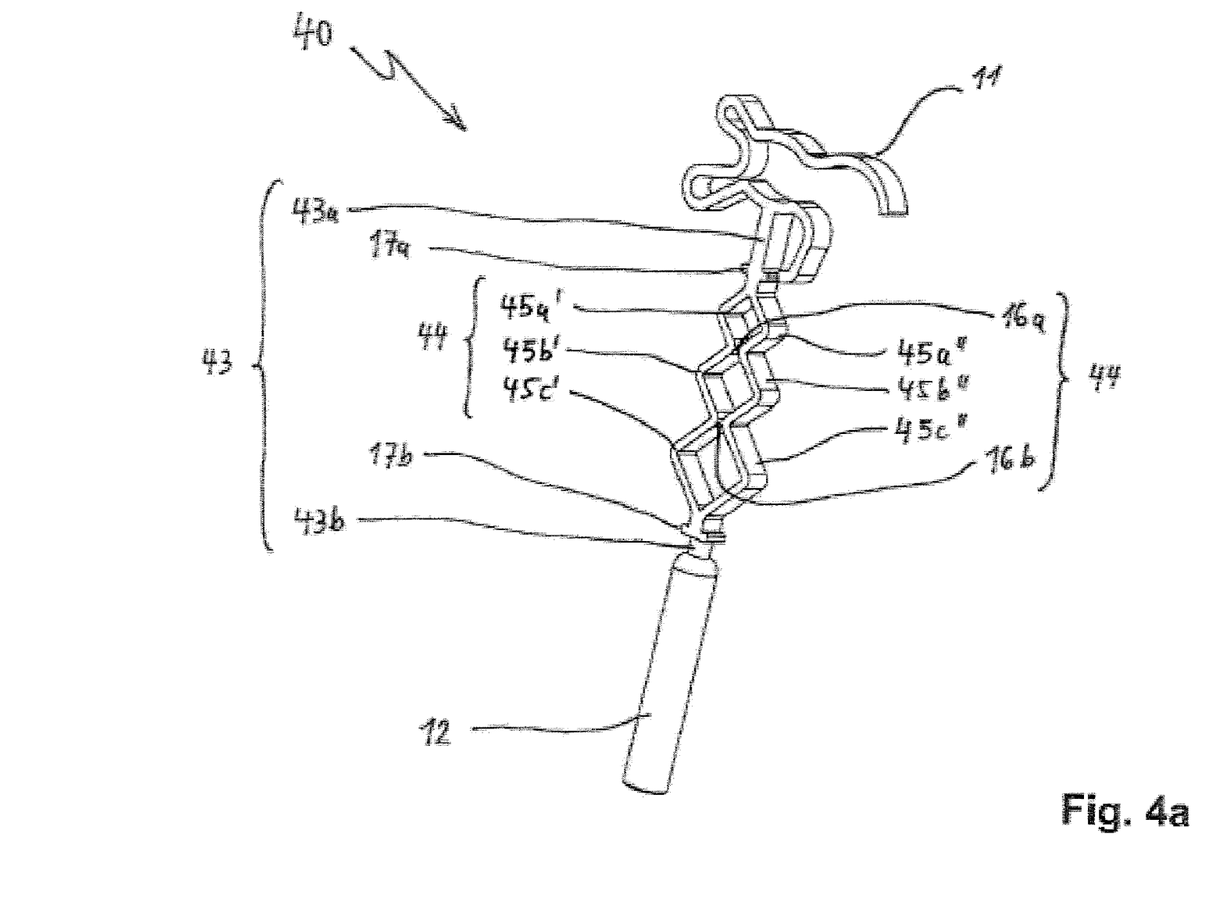
FIGS. 4a,b show an embodiment that includes a clamp-shaped first fastening element, an adjusting device that includes loop pairs that have been pulled apart in the manner of an accordion, and each of which has a different transverse extension, and a piston-shaped second fastening element.
Figure 4B:
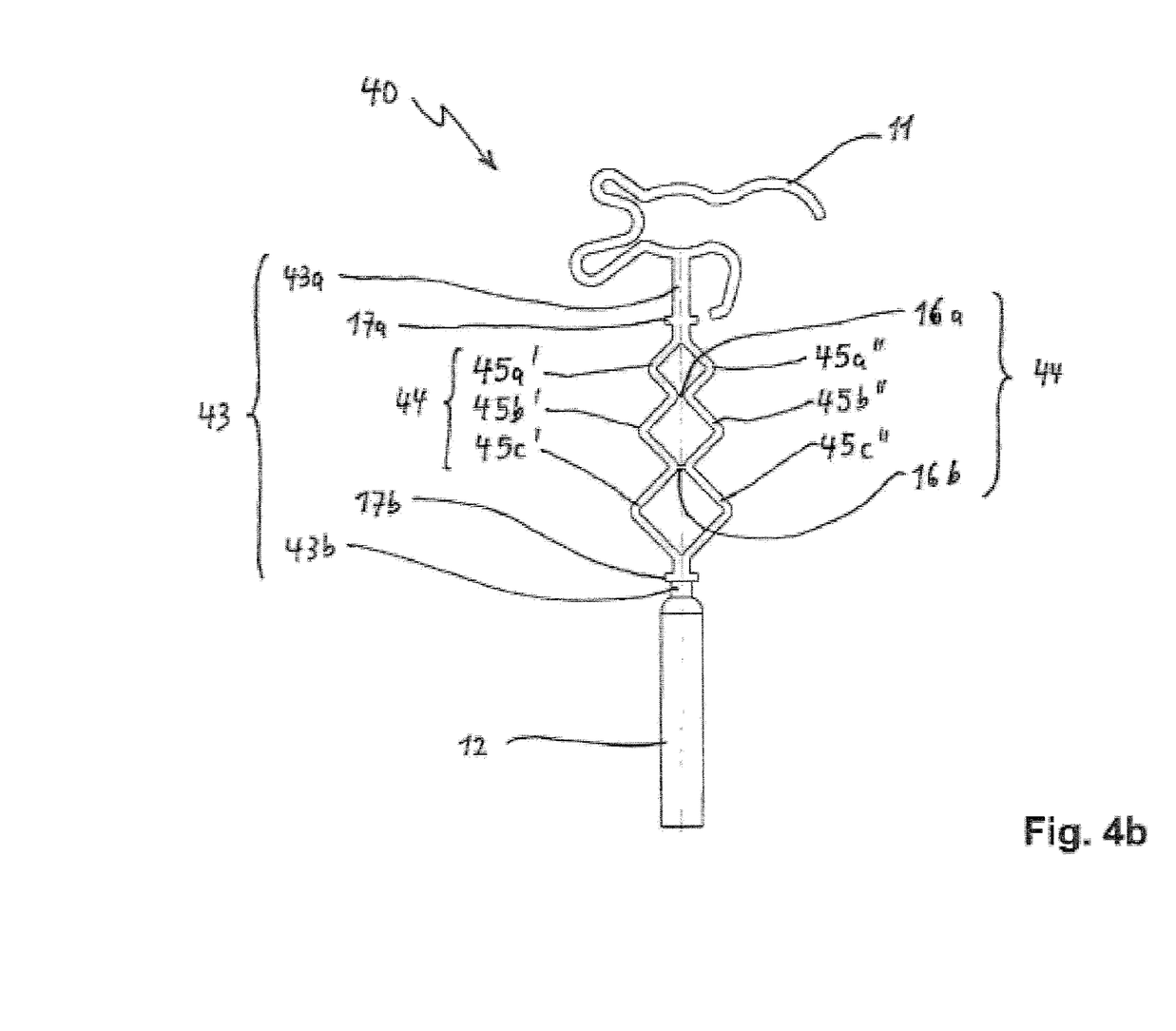

In contrast, in the embodiments shown in FIGS. 2a-b and 3a-b, first fastening element 21 is designed, in each case, in the form of a top plate for placement against the tympanic membrane. In the embodiment of ossicular prosthesis 20 depicted in FIGS. 2a-b, second fastening element 22, on the end opposite the top plate, is designed in the shape of a piston for placement against the base of the stapes, while second fastening element 32, in the embodiment of ossicular prosthesis 30 as depicted in FIGS. 3a-b, is designed as a slotted bell and is preferably used to fasten ossicular prosthesis 30 to the stapes.

In embodiments of the ossicular prosthesis, according to the present invention, that are not shown in the drawing, the fastening elements may be designed differently, e.g., as a sleeve, loop or hook. The second fastening element may also be designed, e.g., in the form of a clamp.

Elongated connecting element 13; 23; 43; 53 is typically designed as a two-pieced shank, as shown in the embodiments depicted in FIGS. 1a-b, 2a-b, 4a-b and 5a-b. In this case, adjusting device 14; 24; 44; 54 is integrated in the shank, and a connecting piece 13a; 23a; 43a; 53a or 13b; 23b; 43b; 53b for first fastening element 11; 21 or second fastening element 12; 22, respectively, is located at both axial ends of adjusting device 14; 24; 44; 54. In the embodiment depicted in FIGS. 3a-b, however, adjusting device 34 itself forms elongated connecting element 33.

As shown in the embodiments depicted in FIGS. 1a-b and 2a-b, loops 15a', 15b', 15c', 15a", 15b", 15c"; 25a', 25b', 25c', 25a", 25b", 25c" of adjusting device 14; 24 may be folded tightly together in the basic state of ossicular prosthesis 10; 20. They are then pulled apart by an operating surgeon in the direction of longitudinal axis a of elongated connecting element 13; 23 in order to attain a desired axial length of the prosthesis, and, once the prosthesis has been implanted in the patient's middle ear, the loops remain, plastically deformed, in this pulled-apart state.

As an alternative, and as shown in the embodiments depicted in FIGS. 3a-b, 4a-b and 5a-b, loops 35a', 35b', 35c', 35a", 35b", 35c"; 45a', 45b', 45c', 45a", 45b", 45c" of adjusting device 34; 44; 54 may be pulled apart in the delivered state of ossicular prosthesis 30; 40; 50, and they are compressed in the direction of longitudinal axis a of elongated connecting element 33; 43; 53 in order to attain the desired axial length of the prosthesis.

The embodiments depicted in FIGS. 1a-b, 3a-b, and 5a-b are also characterized by the fact that loops 15a', 15b', 15c', 15a", 15b", 15c"; 35a', 35b', 35c', 35a", 35b", 35c" of adjusting device 14; 34; 54 have the same maximum extension transversely to longitudinal axis a of elongated connecting element 13; 33; 53. In contrast, in the embodiments depicted in FIGS. 2a-b and 4a-b, axially opposed loop pairs 25a', 25a", 25b', 25b", 25c', 25c"; 45a', 45a", 45b', 45b", 45c', 45c" of adjusting device 24; 44 have maximum extensions that differ transversely to longitudinal axis a of elongated connecting element 23; 24, in particular that continually increase or decrease from one axial end of adjusting device 24; 44 to the other axial end.

Figure 5A:
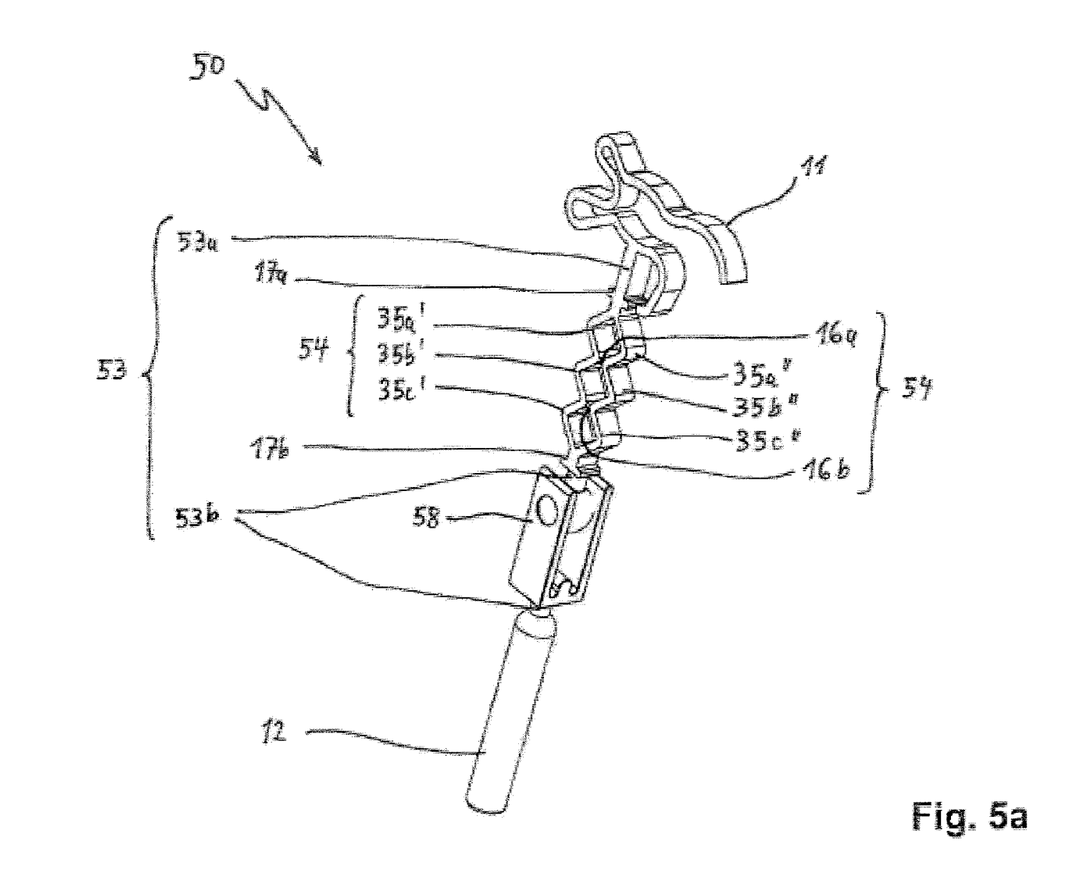
FIGS. 5a,b show an embodiment as depicted in FIG. 4a, but including loop pairs that each have the same transverse extension, and including a ball joint in the connecting element.
Figure 5B:
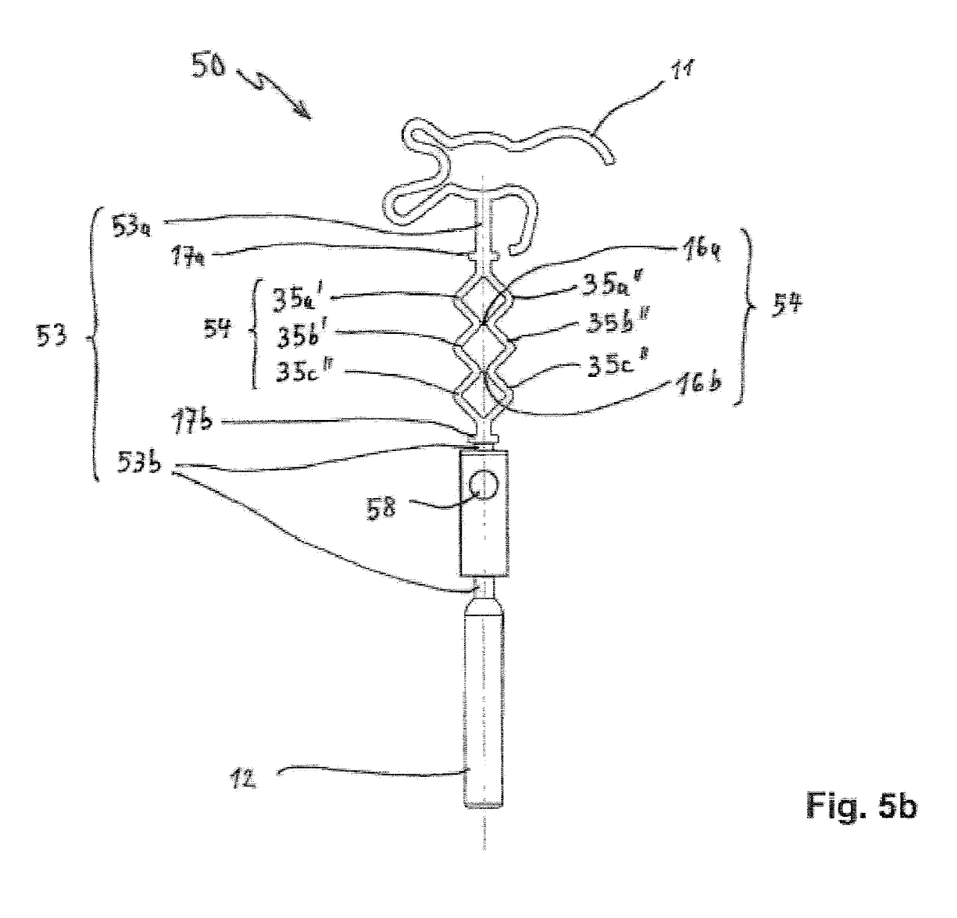

In the embodiment depicted in FIGS. 5a-b, a ball joint 58 is integrated in connecting element 53 in order to attain a certain level of post-operative flexibility of ossicular prosthesis 50 between its connection points.

The mass distribution of the individual parts of ossicular prosthesis 10; 20; 30; 40; 50, according to the present invention, may be calculated as a function of a desired, specifiable frequency response of sound conduction in the middle ear such that it is possible to tune the sound propagation properties in an individualized manner.

It will be understood that each of the elements described above, or two or more together, may also find a useful application in other types of constructions differing from the types described above.

While the invention has been illustrated and described as embodied in a variable-length ossicular prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. An ossicular prosthesis, for replacing or bridging at least one component of a human ossicular chain, comprising a first fastening element provided at one end and mechanically connectable to a tympanic membrane or a component of the ossicular chain; a second fastening element provided at another end and mechanically connectable to a further component or parts of a component of the ossicular chain, or directly to an inner ear; an elongated connecting element which connects said first and second fastening elements in a sound-conductive manner and includes an adjusting device for adjusting an axial length of the ossicular prosthesis in an axial direction of said elongated connecting element, wherein said first fastening element is mechanically rigidly connected to said one end, while said second fastening element is mechanically rigidly connected to another axially opposed end of said connecting element, wherein said adjusting device includes at least two partial strands that extend symmetrically to a longitudinal axis of said connecting element, wherein said at least two partial strands are strands selected from the group consisting of strands extendable in the axial direction, strands compressible in the axial direction, and both, wherein said at least two partial strands are permanently plastically deformable and are folded into a plurality of loops transversely to said longitudinal axis of said connecting element before being deformed.

2. The ossicular prosthesis as defined in claim 1, wherein at least one connecting segment extends transversely to said longitudinal axis and connects one loop of one of said partial strands to a loop of another of said partial strands which is parallel to said one partial strand.

3. The ossicular prosthesis as defined in claim 1, wherein a plurality of connecting segments extend transversely to said longitudinal axis and connect one loop of one of said partial strands to a loop of another of said partial strands which is parallel to said one partial strand.

4. The ossicular prosthesis as defined in claim 1, wherein each of said partial strands includes at least three loops.

5. The ossicular prosthesis as defined in claim 1, wherein in a delivered state of the ossicular prosthesis, said loops of said adjusting device are folded tightly together and are pullable apart by an operating surgeon in a direction of said longitudinal axis of said elongated connecting element to attain a desired axial length of the prosthesis, and, once the prosthesis has been implanted in a patient's middle ear, said loops remain, plastically deformed, in their pulled-apart compressed state.

6. The ossicular prosthesis as defined in claim 1, wherein in a delivered state of the ossicular prosthesis, said loops of said adjusting device are pulled apart, are compressible by an operating surgeon in the direction of said longitudinal axis of said elongated connecting element to attain a desired axial length of the prosthesis, and once the prosthesis has been implanted in the patient's middle ear, said loops remain, plastically deformed, in their compressed state.

7. The ossicular prosthesis as defined in claim 1, wherein said loops of said partial strands of said adjusting device are folded in a manner selected from the group consisting of a serpentine manner, a meandering manner, and in an accordion-like manner.

8. The ossicular prosthesis as defined in claim 1, wherein said loops each have a same maximum extension transversely to said longitudinal axis of said elongated connecting element.

9. The ossicular prosthesis as defined in claim 1, wherein said loops of said adjusting device include axially opposed loop pairs having maximum extensions that differ transversely to the longitudinal axis of said elongated connecting element.

10. The ossicular prosthesis as defined in claim 9, wherein said axially opposed loop parts of said adjusting device continually increase or decease from one axial end of said adjusting device to another axial end of said adjusting device.

11. The ossicular prosthesis as defined in claim 1, wherein said elongating connecting element is formed by said adjusting device.

12. The ossicular prosthesis as defined in claim 1, wherein said elongated connecting element is a shank.

13. The ossicular prosthesis as defined in claim 12, wherein said adjusting device is integrated in said shank, and a connecting piece for said first fastening element, and a connecting piece for said second fastening element are located on two axial ends of said adjusting device.

14. The ossicular prosthesis as defined in claim 1, further comprising an engagement device provided on each of two axial ends of said adjusting device, on which a non-positive fit connection or form-fit connection is formed using a condition instrument in order pull said adjusting device apart or compress said adjusting device via application of force, in a direction of said longitudinal axis of said connecting element.

15. The ossicular prosthesis as defined in claim 14, wherein said adjusting device is provided on each of said two axially ends of said adjusting device with an axial clearance to said first fastening element and to said second fastening element.

16. The ossicular prosthesis as defined in claim 1, wherein said connecting element includes at least one joint.

17. The ossicular prosthesis as defined in claim 16, wherein said at least one joint of said connecting element is a joint selected from the group consisting of a ball joint and an axially extending ball joint chain.

18. The ossicular prosthesis as defined in claim 1, wherein at least one of said fastening elements is an element selected from the group consisting of a plate, a top plate for placement against the tympanic membrane, a sleeve, a loop, a hook that is bent round in shape and is partially open, a closed bell, a bell having one slot, a belt having more than one slot, and a clip for mechanical connection to a component of the ossicular chain.

19. The ossicular prosthesis as defined in claim 1, wherein said second fastening element is a piston which couples the ossicular prosthesis directly to the inner ear in a manner selected from the group consisting of via perforation of stapes by stapedectomy or stapedotomy, via opening up a human cochlea or cochleotomy, and both.

20. The ossicular prosthesis as defined in claim 1, wherein said first fastening element is an element which fastens the ossicular prosthesis to the tympanic membrane at one end, while said second fastening element is an element which fastens the ossicular prosthesis to an incus or stapes at another end.

21. The ossicular prosthesis as defined in claim 1, wherein at least parts of the ossicular prosthesis are composed of biocompatible plastics selected from the group consisting of silicone, polytetrafluorethylene, polyetheretherketone, a fibrous composite material, and carbon fibers.

22. The ossicular prosthesis as defined in claim 1, wherein at least parts of the ossicular prosthesis are composed of a material selected from the group consisting of titanium, gold, tantalum, an alloy of titanium, an alloy of gold, and an alloy of tantalum.

23. The ossicular prosthesis as defined in claim 1, wherein at least parts of the ossicular prosthesis are composed of a material that has memory effect.

24. The ossicular prosthesis as defined in claim 23, wherein said at least parts of the ossicular prosthesis are composed of Nitinol.

25. The ossicular prosthesis as defined in claim 23, wherein at least parts of the ossicular prosthesis are composed of a ceramic material.

* * * * *